(12) United States Patent
Hynes et al.

(10) Patent No.: US 7,607,554 B2
(45) Date of Patent: Oct. 27, 2009

(54) PERISTALTIC PRECISION METERING DEVICE, SYSTEM AND METHOD OF USE THEREOF

(75) Inventors: Anthony J. Hynes, Burnt Hills, NY (US); Randall E. Allen, Troy, NY (US)

(73) Assignee: Precision Valve and Automation, Inc., Halfmoon, NY (US)

( * ) Notice: Subject to any disclaimer, the term of this patent is extended or adjusted under 35 U.S.C. 154(b) by 283 days.

(21) Appl. No.: 10/631,103

(22) Filed: Jul. 31, 2003

(65) Prior Publication Data
US 2005/0023291 A1 Feb. 3, 2005

(51) Int. Cl.
*B67D 5/08* (2006.01)
(52) U.S. Cl. .................. 222/63; 222/101; 222/207; 222/504; 222/45; 222/325; 604/153
(58) Field of Classification Search ............... 222/63, 222/214, 333, 325, 209, 527, 529, 101, 102, 222/207, 181.2, 504, 52; 604/153; 417/53, 417/45, 63
See application file for complete search history.

(56) References Cited

U.S. PATENT DOCUMENTS

| | | | | |
|---|---|---|---|---|
| 1,311,354 A | * | 7/1919 | King, B.W. | 222/101 |
| 2,113,022 A | | 4/1938 | Hefti | 222/207 |
| RE23,434 E | | 11/1951 | Numbers | 141/381 |
| 2,901,147 A | * | 8/1959 | Bond, Jr | 222/102 |
| 3,221,941 A | | 12/1965 | Lott | 222/102 |
| 3,313,454 A | * | 4/1967 | Welsh et al. | 222/102 |
| 3,865,107 A | | 2/1975 | Barton | 604/124 |
| 3,930,761 A | * | 1/1976 | Barraclough | 417/476 |
| 3,946,904 A | * | 3/1976 | Mulakala | 222/102 |
| 3,990,444 A | * | 11/1976 | Vial | 604/67 |
| 4,125,206 A | * | 11/1978 | Wilson | 222/101 |
| 4,256,242 A | * | 3/1981 | Christine | 222/207 |
| 4,349,133 A | | 9/1982 | Christine | 222/183 |
| 4,406,440 A | * | 9/1983 | Kulle et al. | 251/6 |
| 4,482,347 A | * | 11/1984 | Borsanyi | 604/153 |
| 4,493,706 A | * | 1/1985 | Borsanyi et al. | 604/153 |
| 4,585,147 A | * | 4/1986 | Wodnicki | 222/50 |
| 4,667,854 A | | 5/1987 | McDermott et al. | 222/101 |
| 4,671,792 A | * | 6/1987 | Borsanyi | 604/153 |
| 4,820,268 A | * | 4/1989 | Kawamura et al. | 604/67 |
| 4,867,744 A | * | 9/1989 | Borsanyi | 604/153 |
| 4,869,457 A | * | 9/1989 | Ewerlof | 251/6 |
| 5,105,992 A | * | 4/1992 | Fender et al. | 222/52 |
| 5,213,483 A | * | 5/1993 | Flaherty et al. | 417/477.2 |
| 5,377,871 A | | 1/1995 | Banks et al. | 222/41 |

(Continued)

*Primary Examiner*—Patrick F Brinson
(74) *Attorney, Agent, or Firm*—Schmeiser, Olsen & Watts (57) ABSTRACT

The invention relates generally to a peristaltic precision metering device, system and method of using the same. Disclosed is a metering device which includes a metering element that can engage with a compressible material line, wherein the metering device can place a selectable peristaltic effect upon the material in the line. Also disclosed is a metering system comprised of a metering device similar to above and a control system attached to the metering element and a robotic positioning system also attached to the metering device. Finally disclosed is a method of precision material dispensing comprised of providing a metering element and base, positioning a compressible material line between the metering element and base, moving one of the base, metering element, material line, or combination thereof, thereby causing a peristaltic effect upon material in the line, and dispensing a precise unit of material from the device.

24 Claims, 11 Drawing Sheets

U.S. PATENT DOCUMENTS

| | | | |
|---|---|---|---|
| 5,431,307 A | * | 7/1995 | Brown et al. ................. 222/135 |
| 5,611,465 A | * | 3/1997 | Lee et al. .................... 222/214 |
| 5,938,414 A | * | 8/1999 | Kayahara et al. ............ 417/476 |
| 5,939,023 A | | 8/1999 | Coelho et al. ................ 422/101 |
| 6,036,056 A | * | 3/2000 | Lee et al. ...................... 222/63 |
| 6,253,968 B1 | | 7/2001 | Van Dijk et al. ............ 222/241 |

* cited by examiner

PERISTALTIC PRECISION METERING DEVICE, SYSTEM AND METHOD OF USE THEREOF

BACKGROUND OF THE INVENTION

1. Technical Field

The invention relates generally to a device that applies a peristaltic effect to dispense precise amounts of material. A system incorporating the device and a method of using the device are also disclosed.

2. Related Art

In the art of material dispensing systems, efforts for more accurate dispensing devices and systems are continuously being made. Metering accuracy is highly desirous wherein accuracies of actually metering material, for example, within 5% of the desired quantity of metered material are important in certain technologies, such as computer chip underfill dispensing.

Further, the costs of maintenance and cleaning of dispensing systems is highly regarded, as with any manufacturing costs. With most precision metering systems, significant manhours and manufacturing downtime, which translate into costs, must be expended to clean the material dispensing system between dispensing cycles, uses, workshifts, or material changes. Often with material dispensing systems, such as those used in computer chip underfill operations, the entire dispensing end of the system has to be changed out with a second dispensing end when the system has to be cleaned. As a result, a manufacturer is, in essence, forced to procure and keep at least two dispensing ends on hand per each dispensing system. This is a significant cost because the dispensing ends are typically quite expensive. Some, for example, may cost thousands of dollars.

In the art of underfilling computer chips, many of the aforementioned deficiencies are exacerbated because underfill material typically has a short pot life and is also very expensive.

Another deficiency with the use of underfill material in dispensing systems, is that because the fillers (e.g., quartz, silica, glass-based materials, etc.) used in the underfill material have scouring properties, the underfill material shortens the life of the dispensing systems that it comes into contact with. In particular, rubber seals, metal, and other dispensing system parts wear out quicker due to the scouring action caused by these fillers.

Thus, a need exists for a precision metering device, system, and method which overcomes these, and other, deficiencies in the art.

SUMMARY OF THE INVENTION

According to the present invention, several of the aforementioned deficiencies, and others in the art are overcome. The present invention relates to an apparatus, system, and method of using the same in the art of precision metering of materials.

In a first general aspect, the present invention provides a metering device comprising:
a metering element, operationally attached for engaging a compressible material line, thereby causing a selectable peristaltic effect upon a material in said compressible material line.

In a second general aspect, the present invention provides a precision metering system comprising:
a material delivery unit including:
    a material reservoir, a material dispensing end, and a compressible material line connecting said material reservoir and said material dispensing end;
a base;
a metering element, adapted to engage said compressible material line between said metering element and said base, thereby creating a peristaltic effect upon a material in said compressible material line, said peristaltic effect thereby causing a precision dispensing of a unit of material from said material dispensing end, wherein said unit of material is selectable.

In a third general aspect, the present invention provides a metering device comprising:
a metering element that is one of slidable and rotatable, operationally attached for engaging a compressible material line, and upon said sliding or rotation causes a peristaltic effect upon a material located within said compressible material line further causing a precision dispensing of a unit of material from said device.

In a fourth general aspect, the present invention provides a metering system comprising:
a metering device including:
    base;
    a metering element, adapted for engaging a compressible material line positioned between said metering element and said base, thereby causing a peristaltic effect upon a material in said compressible material line;
    a control system operatively attached to said metering element, wherein said control system allows for control of said metering element; and
    a robotic positioning system operatively attached to said metering device.

In a fifth general aspect, the present invention provides a method of precision dispensing of material comprising:
providing a device which includes a base; and
a metering element;
positioning a compressible material line between said metering element and said base;
moving one of said base, metering element, compressible material line, or a combination thereof, thereby causing a peristaltic effect upon a material within said compressible material line; and
dispensing a precise unit of material from said device.

The foregoing and other features and advantages of the invention will be apparent from the following more particular description of embodiments of the invention. It is to be understood that both the foregoing general description and the following detailed description are exemplary, but are not restrictive, of the invention.

BRIEF DESCRIPTION OF THE DRAWINGS

Some of the embodiments of this invention will be described in detail, with reference to the following figures, wherein like designations denote like members wherein.

DETAILED DESCRIPTION OF THE INVENTION

Although certain preferred embodiments of the present invention will be shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of an embodiment. The features and advantages of the present invention are illustrated in detail in the accompanying drawings, wherein like reference numerals refer to like elements throughout the drawings.

As a preface to the detailed description, it should be noted that, as used in this specification and the appended claims, the singular forms "a", "an" and "the" include plural referents, unless the context clearly dictates otherwise.

The present invention offers an improved apparatus for accurately dispensing metered materials. Although for purposes of illustration only, an embodiment that can be used for dispensing inter alia computer chip underfill material is disclosed herein. The apparatus and method can be readily used for accurately metering other materials. For example, water, epoxy, or any material where highly accurate, precision, dispensing is required can utilize the present invention. Highly accurate metering of material could be required for technical reasons or financial reasons where the cost of the material dispensed is critical. Another area of technology where precision metering of materials may be required is in the area of medicine.

The present invention is able to dispense material for areas of art wherein precision is required. For example, the present invention is able to dispense within accuracies of ±2% of the desired quantity to be dispensed. This accuracy level is for quantities being dispensed from about 15 mg to about 100 mg. Further, the present invention is able to meter selectable precision quantities of material. That is either the user directly, or via a mechanized, or computerized system, the quantity of metered material can be changed, adjusted, set, varied, etc. based on a pre-determined amount, or adjusted based on a myriad of factors (e.g., costs, environment, etc.).

Figure 2:
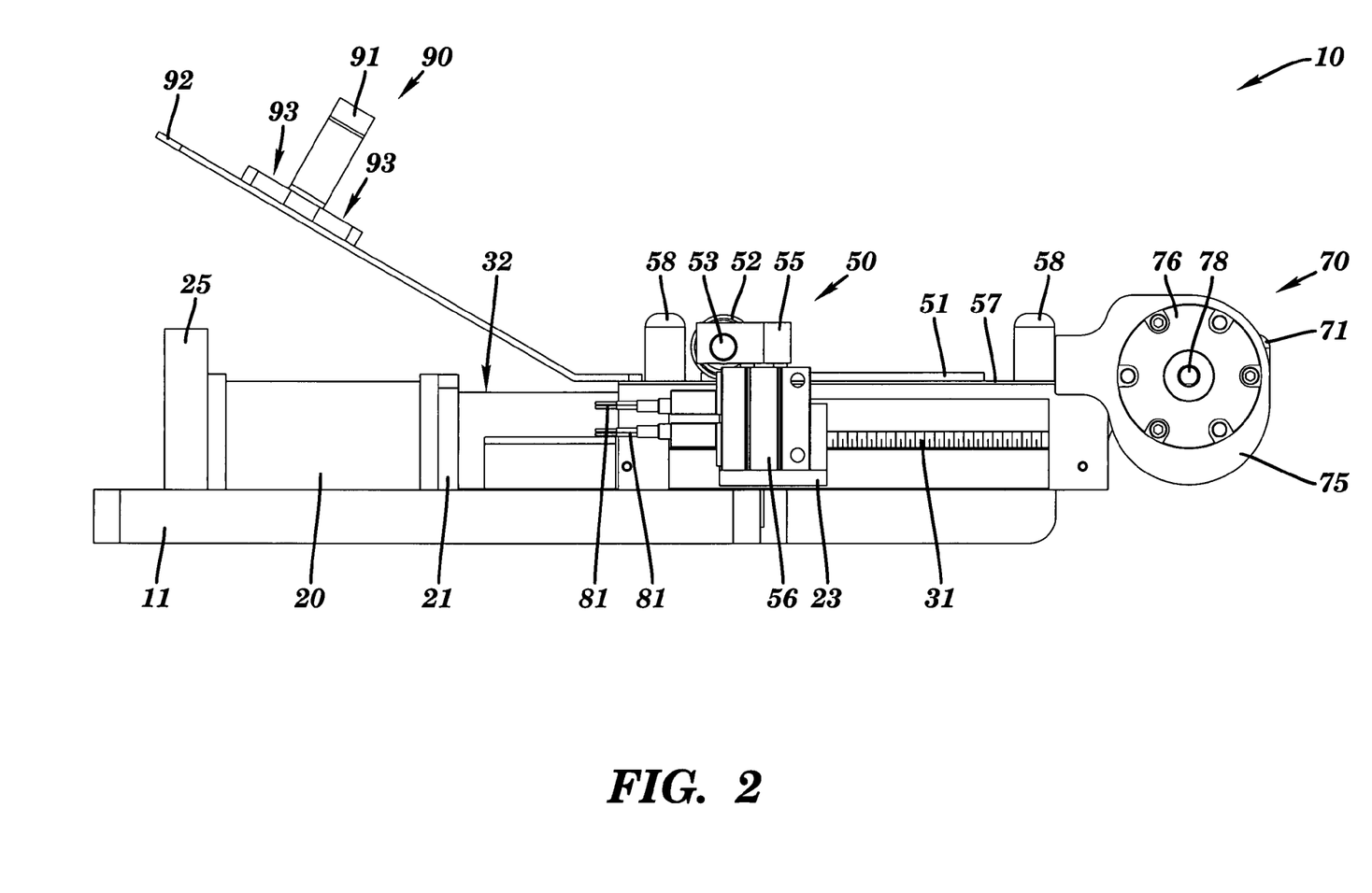
FIG. 2 illustrates a side elevation view of an embodiment of a Peristaltic Precision Metering Device, in accordance with the present invention.
Figure 3:
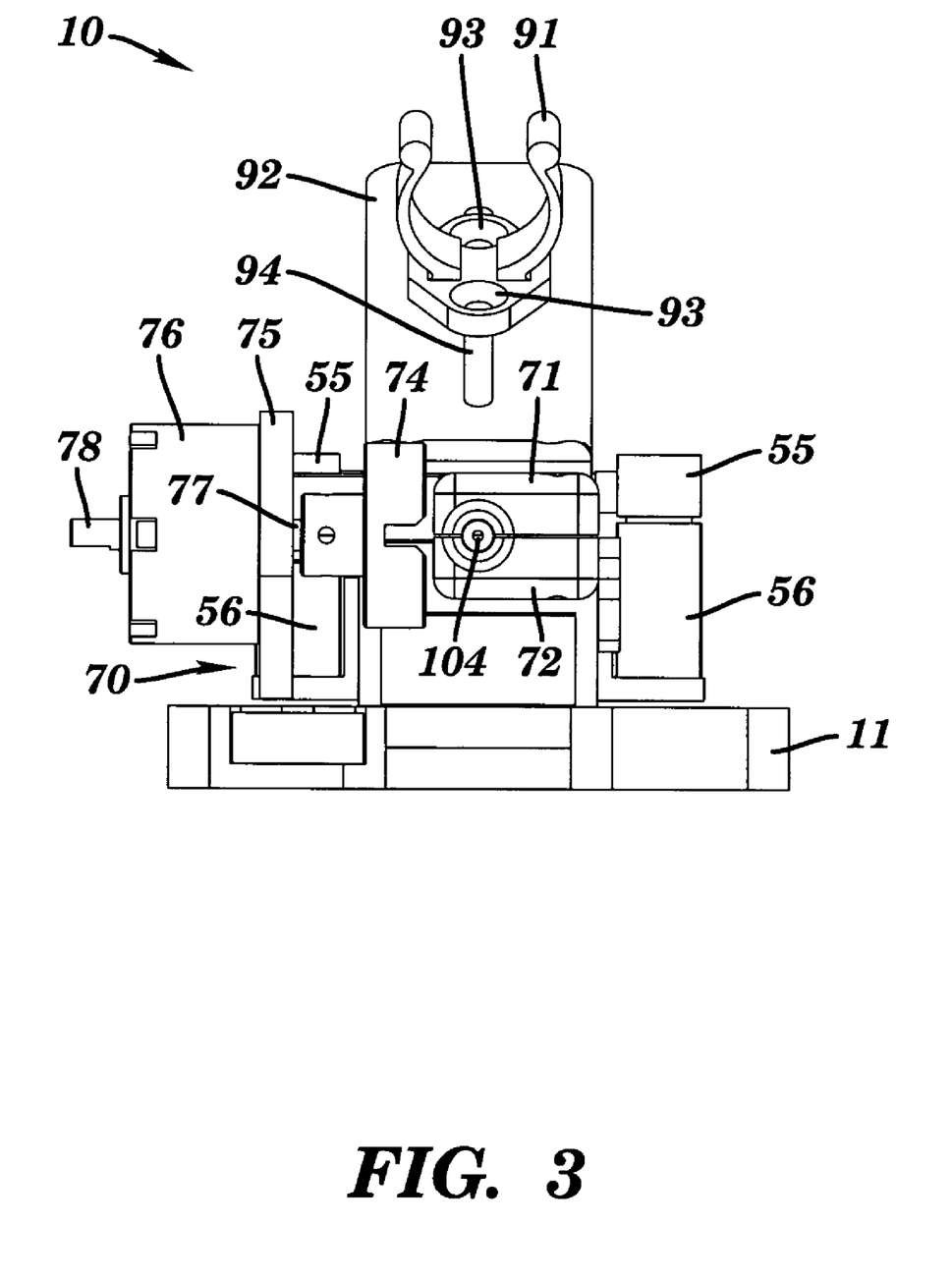
FIG. 3 illustrates a bottom view of an embodiment of a Peristaltic Precision Metering Device, in accordance with the present invention.

Now referring to FIGS. 1, 2, and 3 which illustrate various views of an embodiment of a peristaltic precision metering device, hereinafter referred to as 10. The device, or apparatus, 10 comprises various systems which, together, interact creating a device 10 which is able to dispense precise amounts of material, such as computer chip, or electronics component, underfill, or coating, material, in a way that allows a user to program, prior to and/or during dispensing, the quantity of material to be dispensed. Thus, the user can entirely select (e.g., program, alter, fix, etc.) the desired dispensing amounts. This selectable feature can manual, computerized, mechanized, etc.

The device 10 which may include inter alia a valve actuating system 70, a metering element 50, and a material holding system 90 all attached to a base frame 11. The base frame 11, in turn, can be attached, via screws 12, or other attachment devices, to a robotic positioning system 200 (See e.g., FIG. 9). Further attached to the material holding system 90 is a material delivery system 100 (See e.g., FIG. 4).

Attached to the base frame 11 is a servo motor 20. Typically a size 17 servo motor 20 can be used. Attached at one end of the servo motor 20 is an interface 25, while at the other end of the servo motor 20 is a mount 21. The interface 25 acts as a communication interface between the servo motor 20 and a control system 80 (See e.g., FIG. 11). The mount 21 may be a NEMA® (i.e., National Electrical Manufacturers Association) 14 mount, or other suitable mechanical interface. Beyond the NEMA® 14 mount 21 and interconnected thereto is a ball screw slide 30. On the ball screw slide 30 is a ball screw shaft 31. Thus, rotation of the servo motor 20 causes rotation of a ball screw shaft 31 which, in turn, causes translation of a carriage block mount 23 to which is attached the metering element 50.

The material holding system 90 includes a clamp base 92 which is attached to a guide plate 57. On the clamp base 92 is a slot 94 which allows for a spring clamp 91 to be slidingly attached the base 92 via screws 93.

The metering element 50 includes a pinch roller 52 which is attached to a pinch shaft 53. The ends of the pinch shaft 53 are held within trunnion-like shaft clamps 55. The shaft clamps 55, in turn, are attached to two pneumatic cylinders 56. Extending from the pneumatic cylinders 56 are various sensors 81. The sensors 81 communicate back to a pneumatic system 300 (See e.g., FIG. 11). Typically, Hall-effect sensors can be used. By activating the pneumatic cylinders 56, the pinch roller 52 can be raised away from and/or lowered towards the guide plate 57. Longitudinally running along the guide plate 57 is a depression 60. Spaced on either side of the depression 60 are a pair of roller guides 51. At opposite ends of the guide plate 57 is a tube clamp bracket 58, underneath which is a tube clamp 54. The pinch roller 52 can slide along the depression 60 and guide plate 57 in a translational manner (i.e., slide). The pinch roller 52 may, alternatively, both slide and rotate along the depression 60 and guide plate 57. The guide plate 57, depression 60, and roller guides 51 together act as a type of base in contrast to the metering element 50 above.

At the end distal to the servo motor 20 (i.e. lower end of device 10) is the valve actuating system 70, which is attached to the guide plate 57 and/or frame 11, via a rotary mount 75. To the rotary mount 75 is attached a pneumatic actuator 76 with a pneumatic port 78 which connects to a pneumatic system 300 (See e.g., FIG. 11). Extending from the pneumatic actuator 76 is a rotatable actuator shaft 77 to which is attached a rotary end effector 74.

Also at the lower end of the device 10, and adjacent to the valve actuating system 70 is a ball valve housing, comprised of a ball valve top clamp 71 and a ball valve bottom clamp 72. The housing is attached to the guide plate 57 and/or the frame 11 via a ball valve mount 73. When a material supply system 100 (See e.g., FIG. 4) is installed in the apparatus 10, extending from an opening in both the top clamp 71 and bottom clamp 72 is a material dispensing end. The material dispensing end, in this embodiment, is a dispensing needle 104.

Note that while the embodiment shown indicates that the dispensing end of the apparatus 10 is typically facing downwards, towards the ground (e.g., the material holding system 90 is at the "top" of the apparatus 10), it should be apparent to one skilled in the art, that the apparatus 10 can take on virtually any directional configuration. For example, the apparatus 10 could be placed, during use, in a substantially horizontal configuration, similar to the view shown in FIG. 2.

Figure 4:
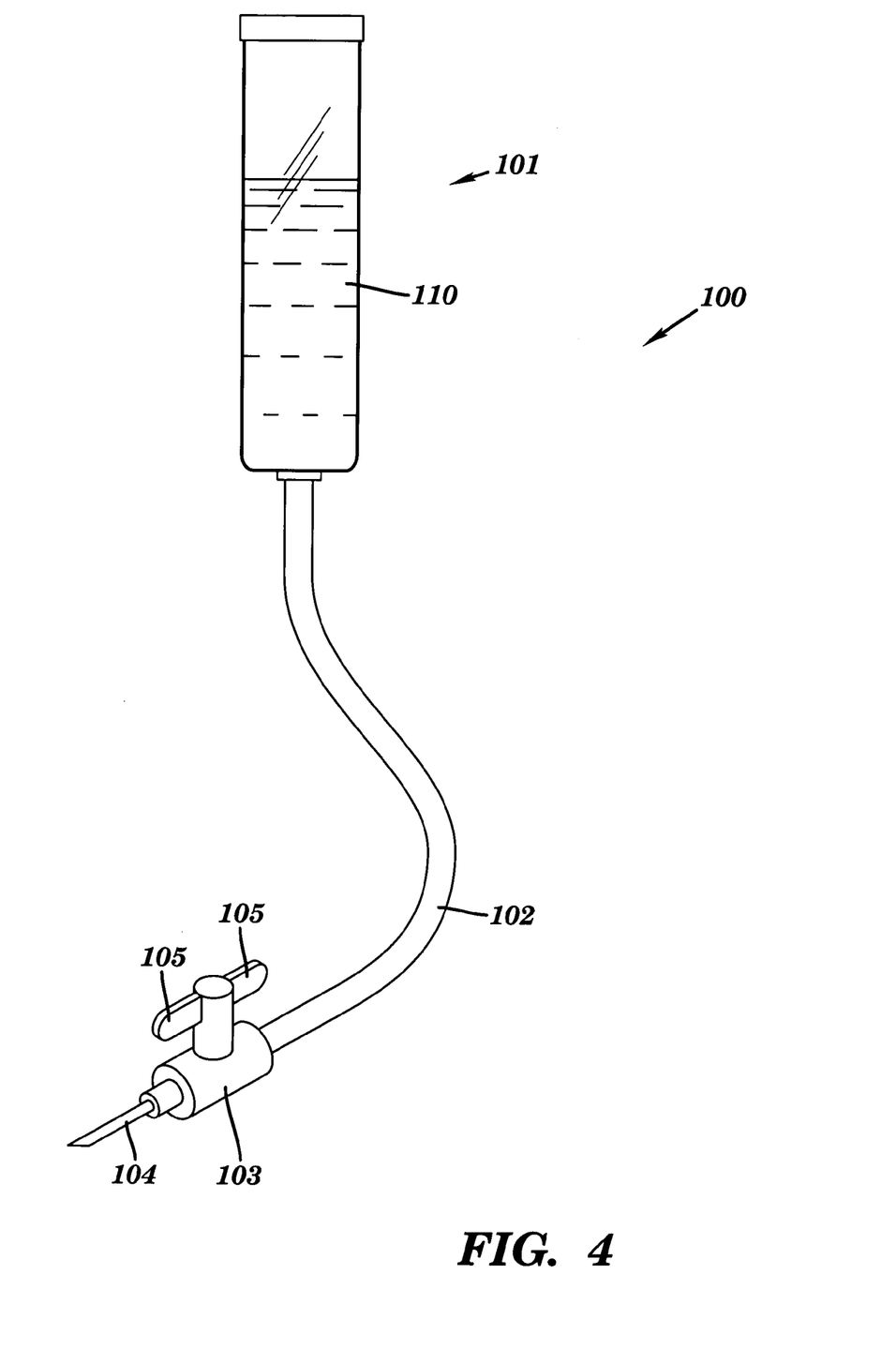
FIG. 4 illustrates a perspective view of material supply system that can be used with an embodiment of the present invention.

Turning to FIG. 4, which illustrates a perspective view of an embodiment of a material supply system 100 that can be used with the device 10. The material supply system 100 can be made of various materials including plastic, glass, rubber, metal, etc. At one end of the material supply system 100 is a material reservoir 101, that holds a quantity of material 110 that is to be dispensed. For example, the material 110 may be computer chip underfill material. At the other end of the material supply system 100 is a dispensing end, which may comprise a dispensing needle 104, from which material 110 is to be dispensed. Adjacent the dispensing needle 104 is a valve, such as a ball valve 103, which has valve handles 105 extending therefrom. Connecting the reservoir 101 to the dispensing needle 104, and allowing communication of material 110 between the two is a material line 102. At least a portion of the material line 102 is compressible, thereby allowing a peristaltic effect to be placed on the material 110 therein caused by the interaction of motion by the metering element 50 upon portions of the material line 110. For example, the material line 110 can be made of inexpensive, flexible plastic tubing. The entire material supply system 100 may be made of inexpensive, disposable materials. Additionally, because the parts of material supply system 100 are the only elements that physically contact the actual material 110 dispensed, no cleaning of parts, changing of parts, or duplicity of parts with the device 10 of the present invention is required.

Figure 1:
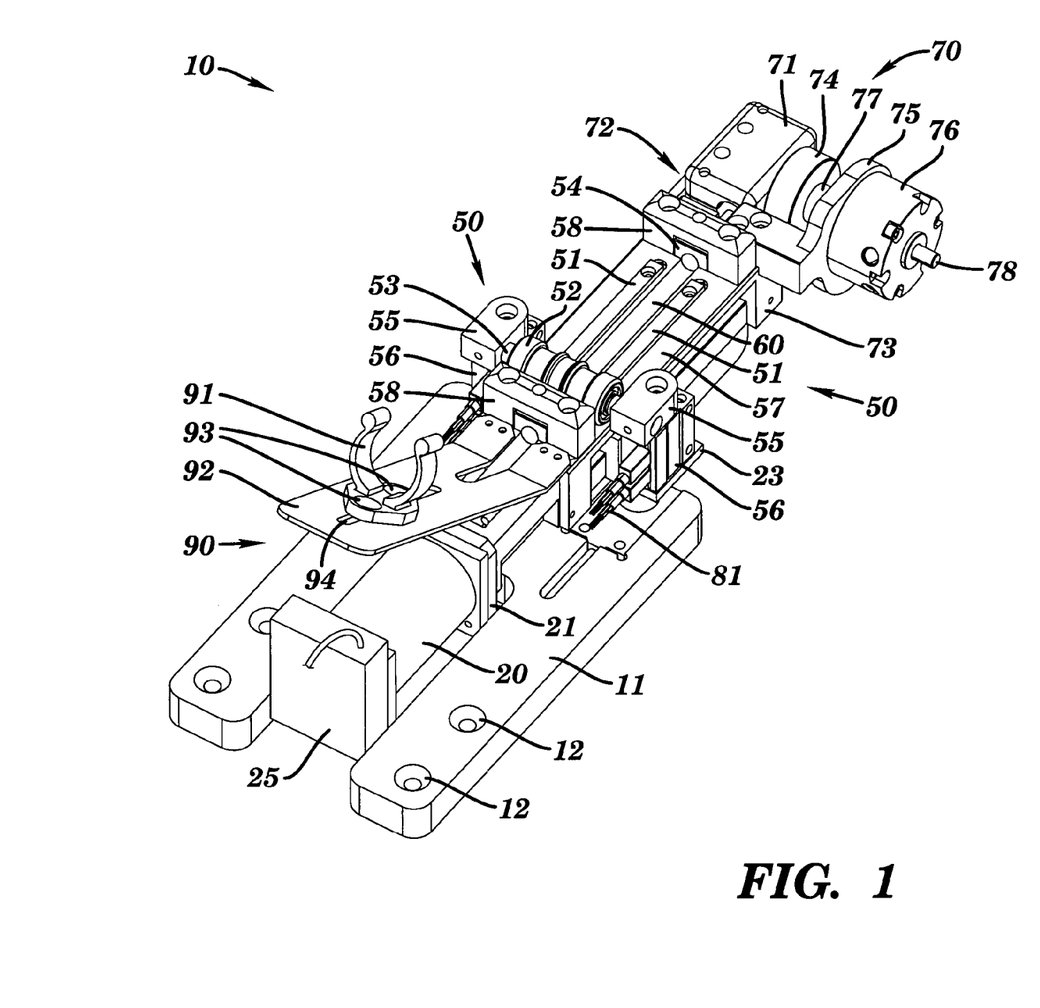
FIG. 1 illustrates a front, upper perspective view of an embodiment of a Peristaltic Precision Metering Device, in accordance with the present invention.
Figure 5:
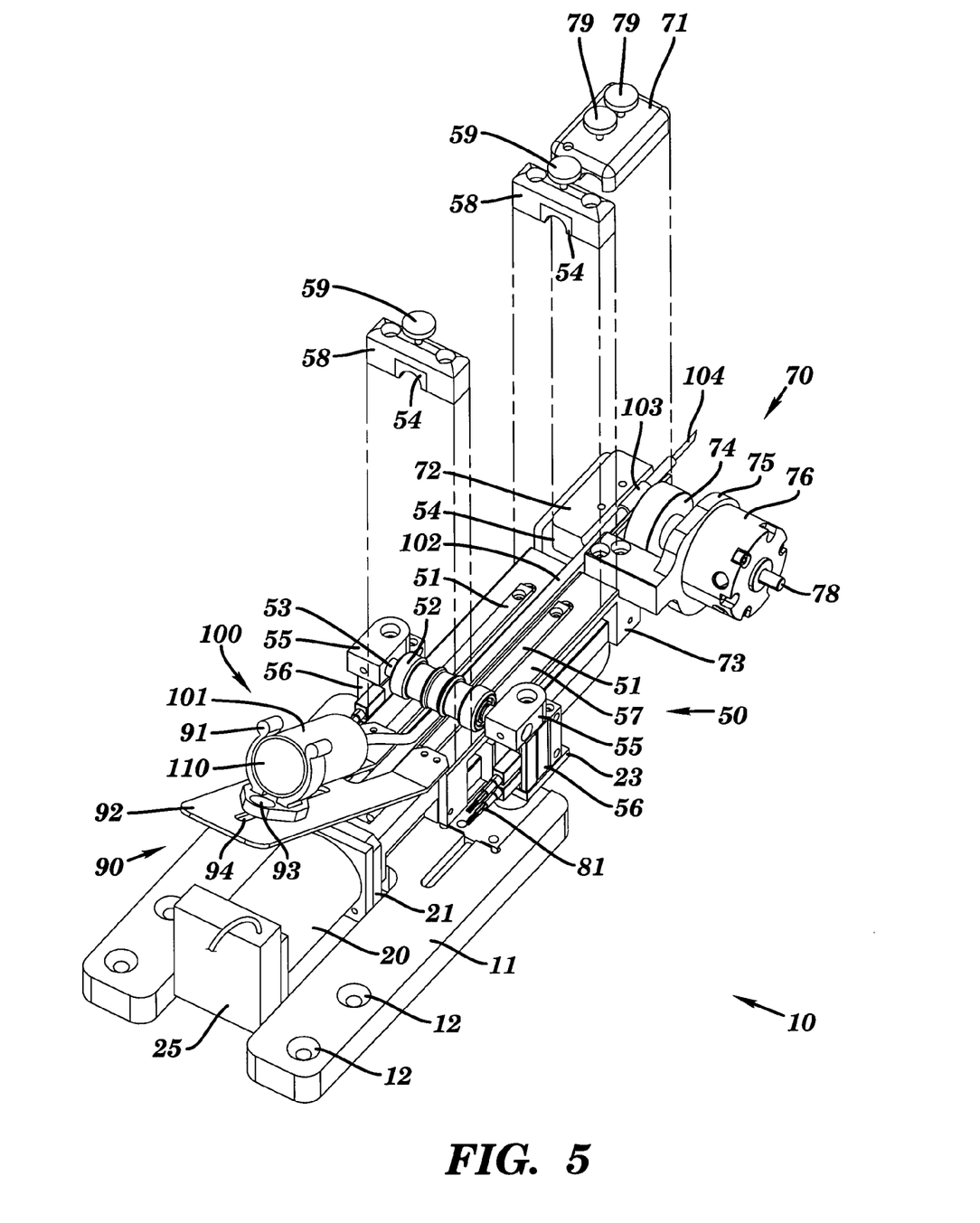
FIG. 5 illustrates the view in FIG. 1, with a partially exploded portion, of an embodiment further employing a material supply system, in accordance with the present invention.

FIG. 5 illustrates the same perspective view shown in FIG. 1 with the addition of the material supply system 100 being installed within the device 10. In order to install, or remove, the material supply system 100, a user can raise the metering element 50 (See e.g., FIG. 7) away from the guide plate 57, in order to gain better access to the guide plate 57 and depression 60. The material reservoir 101 can be placed in the spring clamp 91. The ball valve top clamp 71 is removed from its connection with the ball valve bottom clamp 71, via the loosening of a plurality of thumbscrews 79. Similarly, the two tube clamp brackets 58 and their associated tube clamps 54 are removed from their attachment to the guide plate 57 via thumbscrews 59, as well. Having threaded the tubing 102, ball valve 103, and dispensing needle 104 underneath the metering element 50, the user can now place the tubing 102 on the guide plate 57 and within the depression 60 thereon. Further, the ball valve 103 is placed within the recess of the ball valve bottom clamp 72, so that the ball valve handles 105 are properly disposed within the matching slots located on the rotary end effector 74 (See FIG. 8). Once the ball valve 103 is properly placed within the ball valve bottom clamp 72 with the dispensing needle 104 extending down out of the semi-circular opening in the bottom of the ball valve bottom clamp 72 (See e.g., FIG. 3), the temporarily removed pieces (i.e., tube clamps 54, tube clamp brackets 58, ball valve top clamp 71) may be reinstalled. Prior to the reinstallation of the aforementioned removed pieces, the user may remove slack and/or pre-tension, the tubing 102.

Thus, in order to prepare for dispensing of material 110, the user may first reattach the ball valve top clamp 71 over the ball valve 103 via tightening of the thumbscrews 79 thereby securing the ball valve 103, the dispensing needle 104 and the distal end of the material supply system 100 to the device 10. As shown in FIG. 3, FIG. 5, FIG. 8, and FIG. 9, the dispensing needle 104 is moveably secured into the metering supply system 100 during dispensing. Next the first tube clamp 54 and tube clamp bracket 58 (i.e., proximal to bottom end of the device 10) may be reattached via the thumbscrew 59. Next, the user can reattach the second tube clamp 54 and tube clamp bracket 58 (i.e., near to material holding system 90), via thumbscrew 59, to the guide plate 57, while at the same time, pulling the tubing 102 away from the ball valve 103. This pulling of the tubing 102, or pretensioning, helps prevent any moving, crimping, bunching, or sliding of the tubing 102 during the movement of the metering element 50.

Figure 7:
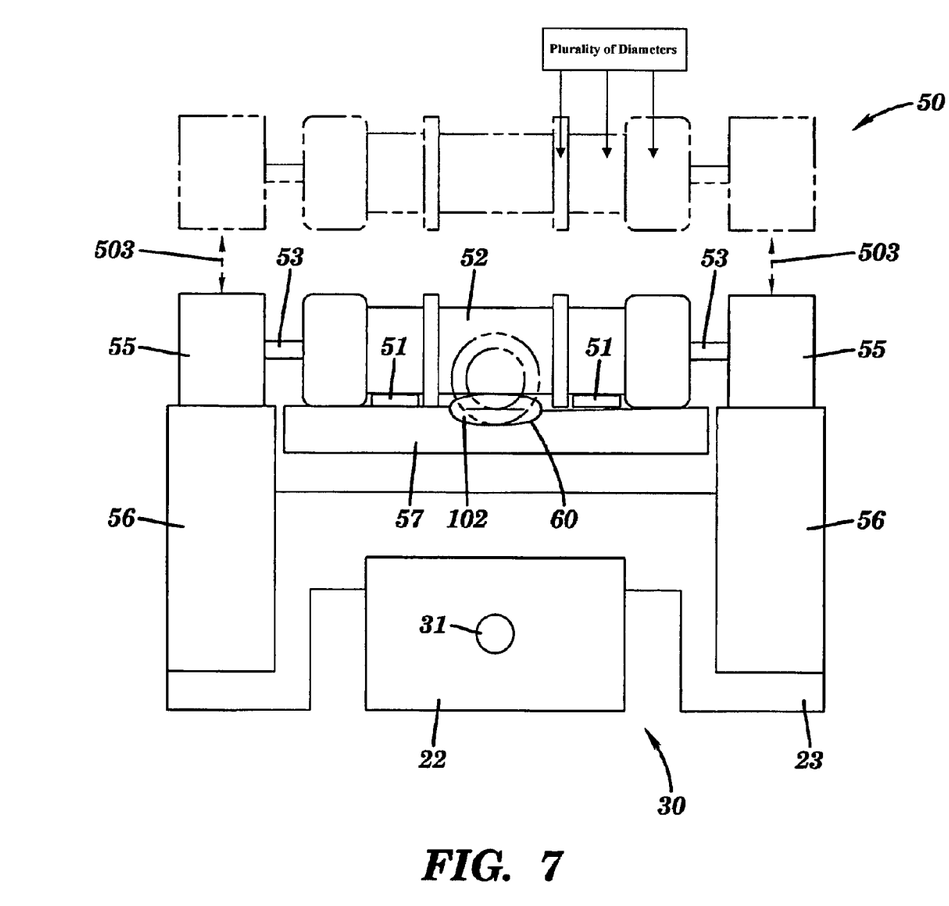
FIG. 7 illustrates a bottom view of a portion of an embodiment of a Peristaltic Precision Metering Device, in accordance with the present invention.

Once the tubing 102, material reservoir 101, and ball valve 103 are held in place, the metering element 50 may be moved down towards the guide plate 57 so that portions of the pinch roller 52 contact the roller guides 51 (see e.g., FIG. 7). The metering element 50 is moved via the actuation of the pair of pneumatic cylinders 56. The movement is denoted by directional arrows 503 (See FIG. 7). When the metering element 50 is moved downward, the center portion of the pinch roller 52 crimps the tubing 102 against the depression 60 in the guide plate 57, such that the tubing 102 is closed.

Figure 6:
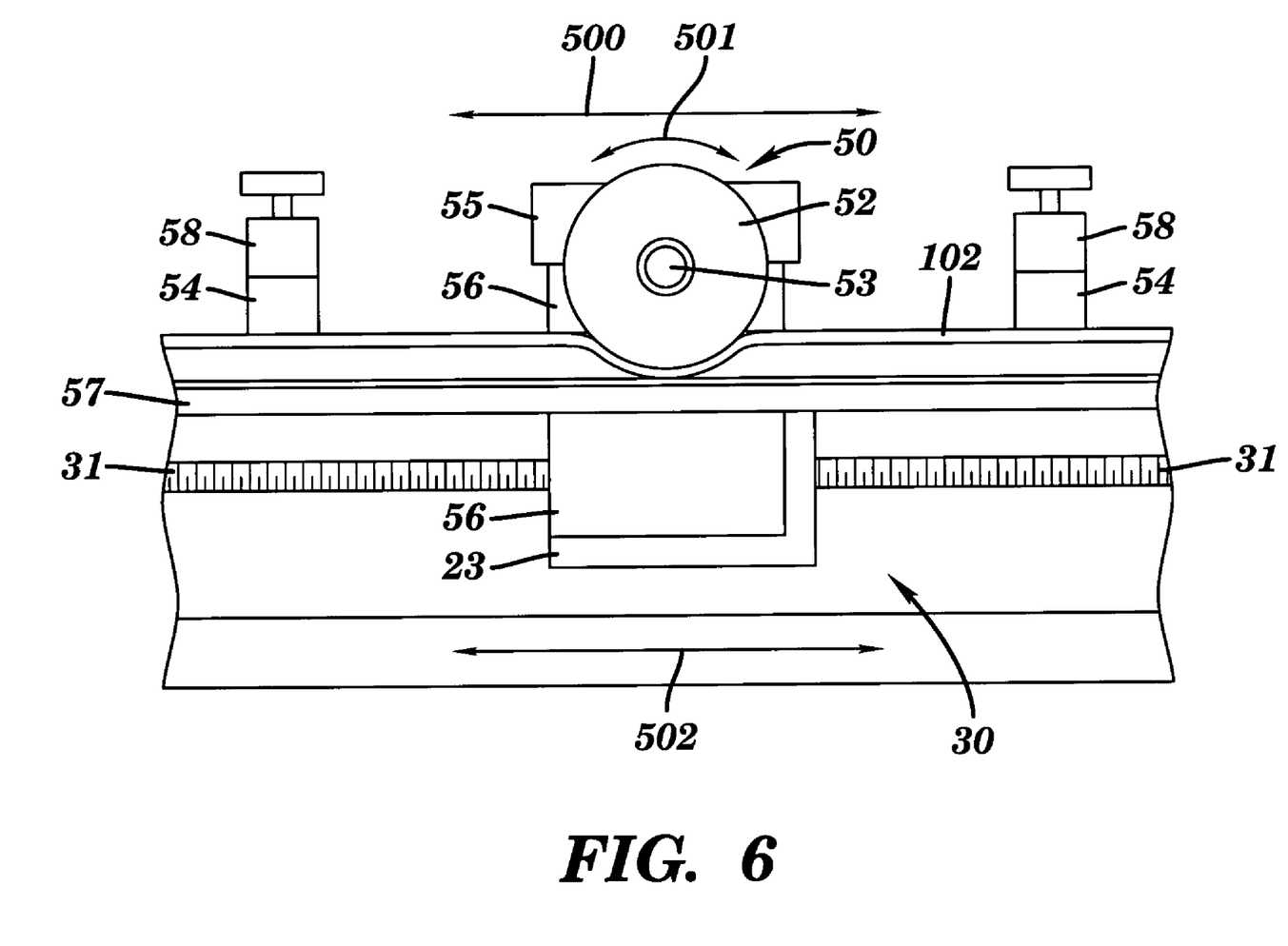
FIG. 6 illustrates a side elevation, sectional view of a squeezing portion of an embodiment of a Peristaltic Precision Metering Device, in accordance with the present invention.

FIG. 6 illustrates a side view of a portion of an embodiment of the apparatus 10 in use. A peristaltic effect is being applied to the tubing 102 by the metering element 50. The carriage block mount 23 moves laterally, denoted by arrow 502, upon rotation of the ball screw shaft 31. As the carriage block mount 23 moves laterally, so does the metering element 50, as denoted by arrow 500. While the metering element 50 moves laterally, the pinch roller 52 also moves laterally. In addition, the pinch roller 52 may rotate about the shaft 53. Rotation is denoted by arrow 501. As the metering element 50 moves laterally along the tubing 102, which is located between the metering element 50 and the base, which is comprised of the glide plate 57, roller guides 57, and depression 60, a peristaltic effect is exerted upon the tubing 102 and the material 110 therein. As the material 110 has exerted upon it a peristaltic effect, the material 110 moves along the tubing 102. The apparatus 10 is able to ultimately dispense a unit of material 110 from the tubing 104. Because the servo motor 20 is able to precisely control the movement of the metering element 50, the apparatus 10 is able to precisely dispense quantities of material 110.

In alternative embodiments, instead of the metering element 50 moving relative to the tubing 102 and guide plate 57, other elements may move to create a similar peristaltic effect. For example, the metering element 50 may be stationary, while the guide plate 57, roller guides 51, depression 60, and possibly other parts of the apparatus 10 move. Similarly, in another embodiment, both the metering element 50 and base (i.e., guide plate 57, roller guides 51, depression 60) are stationary, while the tubing 102 is moved laterally therebetween causing the peristaltic effect.

For example, a user either through prior use, or by trial and error, or by other methods, can calculate to very precise tolerances what quantity of movement (e.g., lateral and/or rotation) of the metering element 50 causes the resultant precision dispensing of a quantity of material 110 from the apparatus 10. The method of calculating these quantities could likewise be done via a computer, or other suitable means and methods. As a result, this creates an apparatus which ultimately allows the user to select the precise quantity for dispensing i.e., selectable dispensing. This selectable dispensing is, in turn, caused by a selectable peristaltic effect placed upon the material 110 in the material line 102. Thus, aside from the aforementioned lateral or rotational movement of the metering element 50, other factors can also affect the quantity of peristaltic effect created. For example, how tightly the metering element 50 is placed against the material line 102, temperature, speed of movement of the metering element 50, type of tubing used for the material line 102, type of underfill material, etc. can all also affect the peristaltic effect.

FIG. 7 shows a close up view of an embodiment of the metering element 50. The pneumatic cylinders 56 can raise and lower the metering element 50, denoted by motion arrows 503. The metering element 50 and tubing 102 in a raised position is shown in phantom, while the metering element 50 and tubing 102 in a lowered position is shown in solid lines. When the metering element 50 is in the lowered position the compressible portion of the tubing 102 is pinched so that an opening in the tubing 102 is now closed. The depression 60 helps fit the contour of the tubing 102 during the lowered position. Additionally, portions of the pinch roller 52 contact the roller guides 52 during the lowered position. The peristaltic effect is placed upon the tubing 102 motion of the metering element 50 in the lowered position. The raised position allows for installation and removal of the material supply system 100 and for motion of the metering element 50 without imparting a peristaltic effect upon the tubing 102 (e.g., resetting the apparatus 10).

Although FIGS. 6 and 7 show a pinch roller 52 being generally cylindrical in shape with multiple diameters, various shapes and configurations can be used for the metering element 50. For example, the metering element 50 can be any arcuate shape. Alternatively, the metering element 50 could, in essence, be any of any shape and volume, in which an precise, effective peristaltic force can be effected on the material 110.

Figure 8:
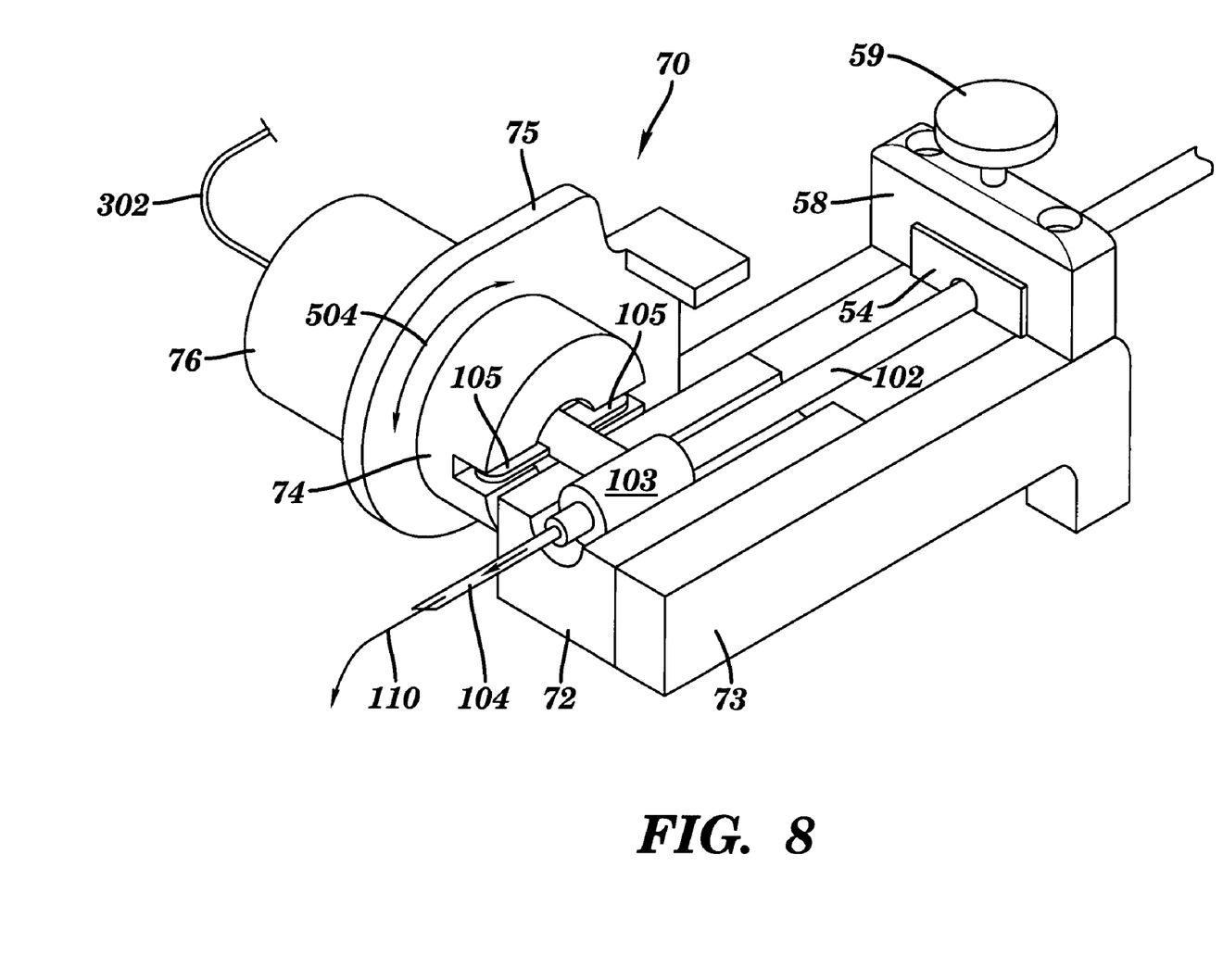
FIG. 8 illustrates a front, lower perspective view of a valve portion of an embodiment of a Peristaltic Precision Metering Device, in accordance with the present invention.

FIG. 8 shows a close-up of an embodiment of the valve actuating system 70 portion of the present invention in use. The ball valve handles 105 are engaged with slots in the rotary end effector 74. The pneumatic actuator 76 is connected via a pneumatic line 302 to a pneumatic system 300 (See e.g., FIG. 11). Upon pneumatic activation, the pneumatic actuator 76 rotates the actuator shaft 77. The rotation of the actuator shaft 77, in turn, causes rotation of the rotary end actuator 76. Rotation of the rotary end actuator 76 is denoted by directional arrow 504. Thus, if ball valve 103 is open, material 110 can be dispensed from the dispensing needle 104. Similarly, if a user desires to close the ball valve 103, the pneumatic actuator 76 can be pneumatically actuated via the pneumatic line 302. The rotation 504 of the rotary end effector 74 will turn the ball valve handles 105 which, in turn, close the ball valve 103.

Figure 9:
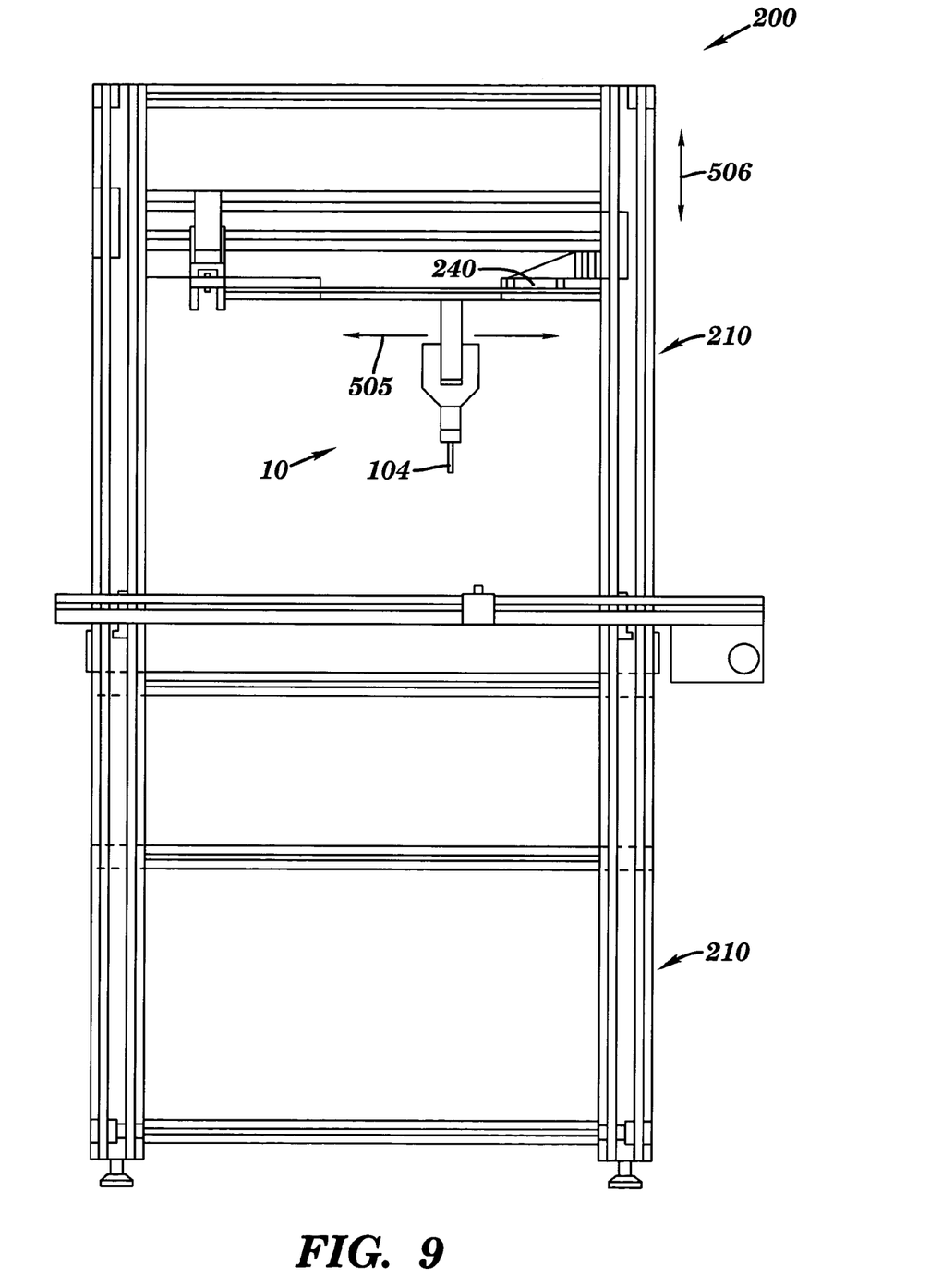
FIG. 9 illustrates a front elevation view of an embodiment of a Peristaltic Precision Metering System, in accordance with the present invention.
Figure 10:
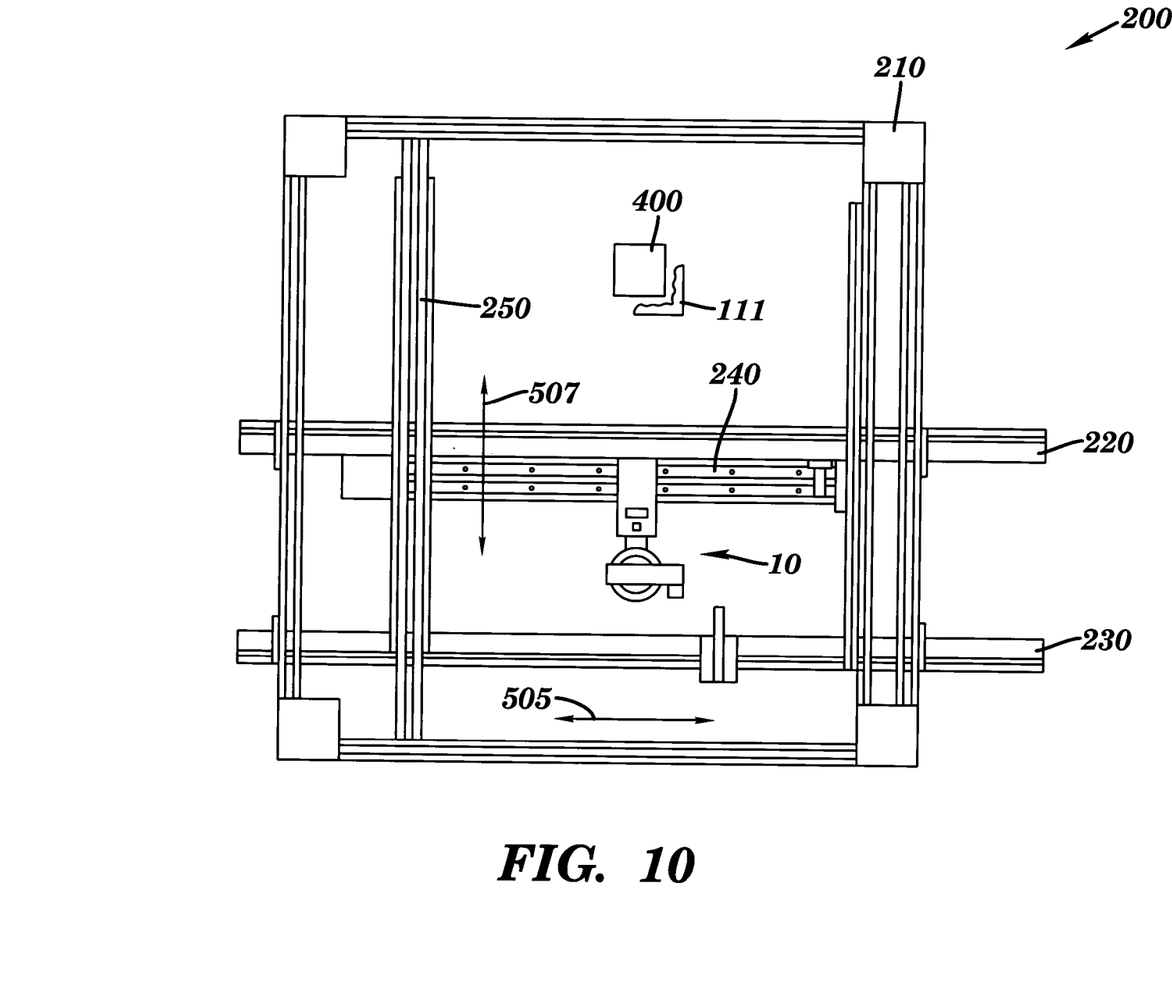
FIG. 10 illustrates a top view of the embodiment in FIG. 9.

FIGS. 9 and 10 depict an embodiment of the present invention in which a robotic positioning system 200 is operatively attached to the apparatus 10. The robotic positioning system 200 includes a gantry frame 210 to which is attached Y axis ball screw slide 250, X axis ball screw slide 220 and the apparatus 10. The apparatus 10 is able to move via the X axis ball screw slide 220 along an X-axis, denoted by directional arrow 505. Similarly, the apparatus 10 is able to move via the Y-axis ball screw slide 250 along a Y-axis, denoted by directional arrow 507. Thus, the apparatus 10 and the dispensing needle 104 thereon is able to be positioned, and moved, within a X-Y plane and dispense material 110, for example, in a material bead 111 for underfill material 110 around a computer chip 400, or other workpiece. The apparatus 10 can similarly be raised and lowered in a Z-axis, the motion denoted by directional arrow 506.

Figure 11:
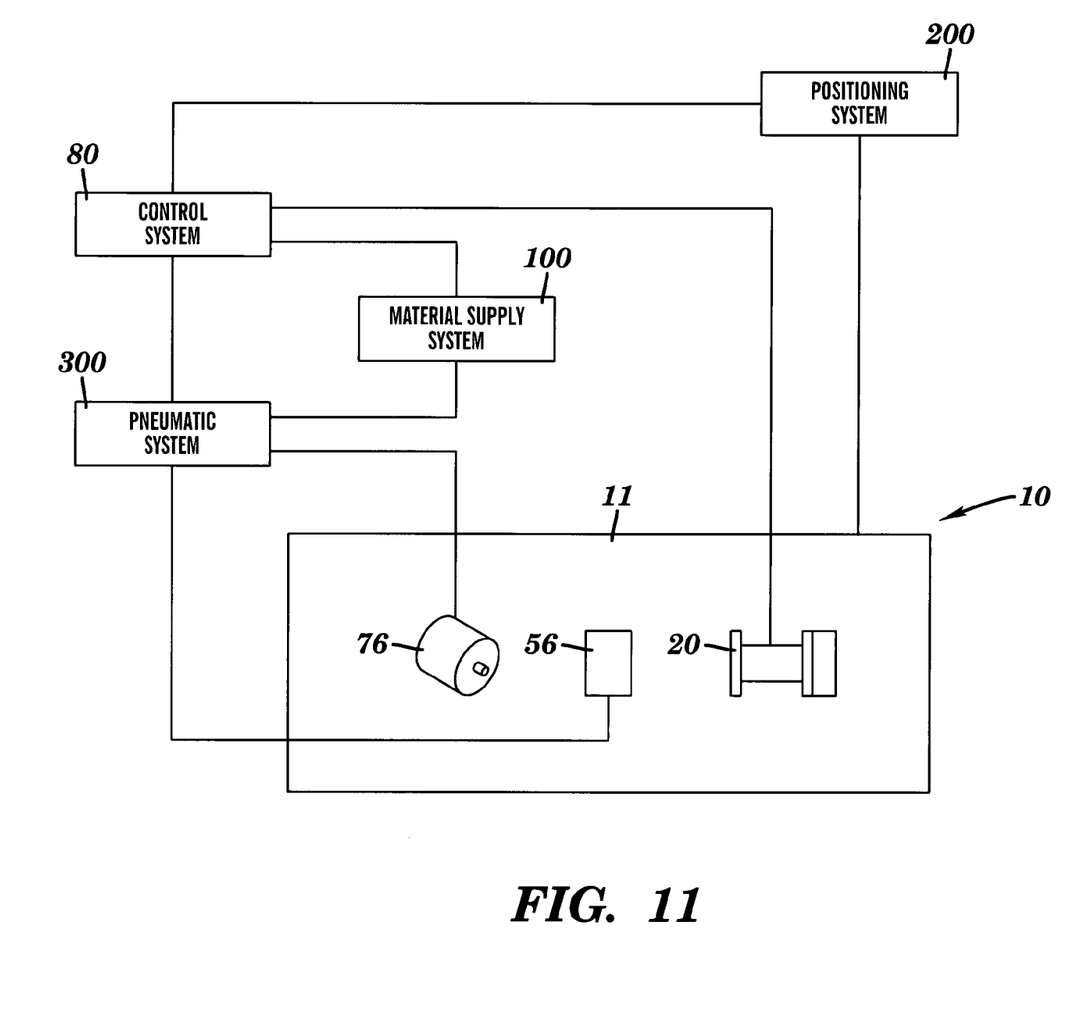
FIG. 11 illustrates a schematic diagram of an embodiment of a Peristaltic Precision Metering System, in accordance with the present invention.

FIG. 11 depicts a schematic diagram showing an entire system which employs the apparatus 10 and various systems which interact with each other. The apparatus 10 comprises inter alia the pneumatic actuator 76, pneumatic cylinders 56 and a servo motor 20 all attached by some manner to a base mount 11. A control system 80, typically a computerized control system, interacts with a pneumatic system 300, the material supply system 100 and the robotic positioning system 200. Thus, the control system 80 via its interaction with the pneumatic system 300 can control the pneumatic actuator 76 and pneumatic cylinders 56. Similarly, the control system 80 can also control the robotic positioning system 200 which, in turn, controls the 3-dimensional position of the apparatus 10. The control system 80 also controls the servo motor 20 which, in turn, controls the position of the metering element 50. The control system 80 can control the material supply system 100 via control of the pneumatic system 300 and its control of the metering element 50 and ball valve 103. Thus, via the interaction and communication of these various systems 80, 100, 200, 300 and the apparatus 10, a user is able to precisely dispense material from the apparatus 10 onto a workpiece 400. A user may be able to program the entire apparatus 10 via the control system 80. Via this programmability feature of the present invention, a user could, for example, elect what quantity of material to be dispensed, or quantity (e.g., translation and/or rotation) the metering element 50 moves, or some other useful parameter.

While the aforementioned embodiments describe an apparatus 10 with a single metering element 50 and single material supply system 100, it should be apparent to one skilled in the art, that other configurations with different quantities of metering elements 50 and materials 110 can be used in the present invention. For example, instead of a single material reservoir 101, two material supply systems 100 could be used with two metering elements 50. Thus, the two metering elements 50, operatively attached to two material tubes 102 containing two different materials 110 therein, could, for example, rotate and slide at different rates along the base. As a result, the quantity of material 110 dispensed from each of the two different materials 110 could be different. This difference in rate, and quantity dispensed, could correspond to a required ratio of materials 110, like in the example, of certain types of epoxy.

Various modifications and variations of the described apparatus and methods of the invention will be apparent to those skilled in the art without departing from the scope and spirit of the invention. Although the invention has been described in connection with specific embodiments, outlined above, it should be understood that the invention should not be unduly limited to such specific embodiments. Various changes may be made without departing from the spirit and scope of the invention as defined in the following claims.

What is claimed is:

1. A metering device comprising:
   a material reservoir containing coating material;
   a metering element capable of translational and rotational movement, operationally attached to a moveably secure carriage block for engaging a compressible material line, thereby causing a selectable peristaltic effect upon the coating material in said compressible material line, wherein said material reservoir directly communicates with the compressible material line; and
   a material dispensing end, moveably secured to said metering element, for movement with said metering element during dispensing;

a control system operatively attached to said metering element, where said control system allows for control of the selectable peristaltic effect and said metering element.

2. The metering device of claim 1, further comprising a base, said base adapted so that the compressible material line is positioned between said base and said metering element.

3. The metering device of claim 2, wherein said base comprises a depression for engagement with said compressible material line.

4. The metering device of claim 1, wherein said metering element is rotatable.

5. The metering device of claim 1, wherein said metering element is slidable.

6. The metering device of claim 1, wherein said metering element has an arcuate portion.

7. The metering device of claim 6, wherein said metering element is a cylinder.

8. The metering device of claim 7, wherein said metering element is a cylinder of a plurality of diameters.

9. The metering device of claim 1, further comprising the compressible material line.

10. The metering device of claim 1, wherein said material dispensing end is a dispensing needle.

11. The metering device of claim 1, wherein said peristaltic effect causes a dispensing of a unit of material from said metering device.

12. The metering device of claim 11, wherein the quantity of said unit of dispensed material is within 2% of a desired quantity of material to be dispensed.

13. A precision metering system comprising:
a material delivery unit including:
a material reservoir, a material dispensing end, a compressible material line connecting said material reservoir and said material dispensing end, and a valve positioned between the compressible material line and the material dispensing end,
a base in operative communication with the material delivery unit;
a metering element, engaging most of the length of said compressible material line between said metering element and said base, thereby creating a peristaltic effect upon a material in said compressible material line, said peristaltic effect thereby causing a precision dispensing of a unit of material from said material dispensing end, wherein said unit of material is selectable; and
wherein the material dispensing end is moveably secured into the material delivery unit for movement with the metering element during operation.

14. The precision metering system of claim 13, further comprising a control system operatively attached to said metering element, wherein said control system allows for control of said metering element.

15. The precision metering system of claim 13, wherein said metering element is a cylinder.

16. The precision metering system of claim 13, wherein said metering element is rotatable.

17. The precision metering system of claim 13, wherein said metering element is slidable.

18. A metering device comprising:
a metering element that is translationally slidable and rotatable and meters to within +/−2% of a desired quantity of a material to be dispensed;
a rotatable threaded shaft that translationally moves said metering element;
a frame, wherein said metering element is movably attached to said frame; and
a material holding system attached to said frame and configured to hold a reservoir, wherein said reservoir holds a quantity of material, having a compressible line extending from said reservoir, wherein a length of said compressible line is positionable beneath said metering element, and upon said sliding or rotation of said metering element causes a peristaltic effect upon a material located within said compressible material line further causing a precision dispensing of a unit of the material from said device.

19. The metering device of claim 18, further comprising:
a clamp base, wherein said clamp base is positioned above said base.

20. The metering device of claim 18, wherein said metering element is selectable.

21. A method of precision dispensing of material comprising:
providing a device which includes a base, a rotatable threaded shaft and a metering element;
providing a reservoir, wherein said reservoir holds a quantity of material, having a compressible material line extending from said reservoir;
inserting the reservoir into the device;
positioning said compressible material line between said metering element and said base;
moving one of said base, metering element, compressible material line, or a combination thereof, to cause a peristaltic effect upon a material within said compressible material line;
rotating said rotatable threaded shaft causing controlled translation motion of said metering element of a precise unit; and
dispensing said precise unit of said material from said device.

22. The method of claim 21, wherein said metering element is a rotatable cylinder.

23. The method of claim 21, wherein said precise unit of material dispensed is within 2% of a quantity desired to be dispensed.

24. The metering device of claim 18 further comprising:
a pinch roller of said metering element; and
a carriage block attached to said pinch roller wherein the length of the compressible line is positioned beneath said pinch roller of said metering element and wherein said rotatable shaft is a ball screw shaft that operationally engages and translationally moves said carriage block of said metering element.

* * * * *